US008030507B2

(12) United States Patent
Kim et al.

(10) Patent No.: US 8,030,507 B2
(45) Date of Patent: Oct. 4, 2011

(54) TIN AMINO-ALKOXIDE COMPLEXES AND PROCESS FOR PREPARING THEREOF

(75) Inventors: Chang Gyoun Kim, Daejeon (KR); Taek-Mo Chung, Daejeon (KR); Young Kuk Lee, Daejeon (KR); Ki-Seok An, Daejeon (KR); Sun Sook Lee, Daejeon (KR); Beyong Hwan Ryu, Daejeon (KR); Se Jin Jang, Daegu (KR)

(73) Assignee: Korea Research Institute of Chemical Technology (KR)

( * ) Notice: Subject to any disclaimer, the term of this patent is extended or adjusted under 35 U.S.C. 154(b) by 162 days.

(21) Appl. No.: 12/407,526

(22) Filed: Mar. 19, 2009

(65) Prior Publication Data

US 2009/0275770 A1 Nov. 5, 2009

(30) Foreign Application Priority Data

Mar. 20, 2008 (KR) .................. 10-2008-0025858

(51) Int. Cl.
*C07F 7/22* (2006.01)
(52) U.S. Cl. ........................................ 556/81
(58) Field of Classification Search .............. 556/81
See application file for complete search history.

(56) References Cited

FOREIGN PATENT DOCUMENTS

| JP | 51019722 A | 2/1976 |
|----|------------|--------|
| JP | 58110427 A | 7/1983 |
| KR | 10-2006-0092661 | 8/2006 |

OTHER PUBLICATIONS

Zemlyansky et al., Organometallics, vol. 22, No. 8, pp. 1675-1681 (2003).*
T.W.F. Russell et al., Economics of processing thin-film solar cells, J.Vac. Sci. Technol. B2 (4), Oct.-Dec. 1984, pp. 840-844.
Sanjay Mathur et al., Germanium Nanowires and Core-Shell Nanostructures by Chemical Vapor Deposition of [GeC5H5)2], 2004 American Chemical Society, Chemical Mater., vol. 16, May 15, 2004, pp. 2449-2456.
Henry Gerung et al., Anhydrous solution synthesis of germanium nanocrystals from the germanium(II) precursor Ge [N(SiMe3)2I2, The Royal Society of Chemistry, Chem. Commun., Feb. 16, 2005, 1914-1916.
Seigi Suh et al., Synthesis of Tin Oxide Precursors and Related Germanium and Lead Compounds, Department of Chemistry, University of Houston, 1996 American Chemical Society, Mar. 14, 1996, pp. 6164-6169.
A. Watanabe et al., Preparation of germanium thin film by a coating technique using a soluble organogermanium cluster as a precursor, 2001 Kluwer Academic Publishers, Journal of Materials Science Letters 491-493.
S. Veprek et al., Organometallic Chemical Vapor Deposition of Germanium from a Cyclic Germylene, 1,3-Di-tert-butyl-1,3,2-diazagermolidin-2-ylidine, American Chemical Society, Chem. Meter., vol. 8, No. 4, pp. 825-831.
Zemlyansky, Nikolay N., et al., "New Stable germylenes, Stannylenes, and Related compounds. 1. Stable Germanium (II) and Tin (II) compounds M(OCH2CH2NME2)2 (M=Ge, Sn) with Intramolecular coordination metal-Nitrogen bonds. Synthesis and structure", Organometallics 2003, 22, 1675-1681.
Hollingsworth, Nathan, et al., "Synthesis and characterisation of new titanium amino-alkoxides: precursors for the formation of TiO2 materials", The Royal Society of Chemistry, 2008, 631-641.
Wakeshima, et al., "Synthesis of stannous chelate compounds", Chemistry Letters (1972), (4), 325-6, Coden: CMLTAG; ISSN: 0366-7022, 76:21865a, 21868a, 76:135202 CA, XP-002528206, Abstract only (1 page).
Mazhar, et al., "Molecular designing of precursors for chemical vapor deposition", Pakistan Journal of Analytical Chemistry (2003), 4(2), 72-76, 142:189464, XP-002528205, Abstract only (1 page).

* cited by examiner

*Primary Examiner* — Porfirio Nazario Gonzalez
(74) *Attorney, Agent, or Firm* — Cantor Colburn LLP

(57) ABSTRACT

The present invention relates to novel tin amino-alkoxide complexes and a method for preparing the same, precisely novel tin amino-alkoxide complexes represented by formula 1 and useful as a precursor for tin and tin oxide thin films and a precursor for the production of nano-sized tin and tin oxide particles and a method for preparing the same. In formula 1, A is linear or branched (C2-C10) alkylene substituted or not substituted with halogen; $R^1$ and $R^2$ are independently linear or branched (C1-C7) alkyl substituted or not substituted with halogen.

$Sn[O-A-NR^1R^2]_2$    [Formula 1]

8 Claims, 6 Drawing Sheets

【Figure 1】
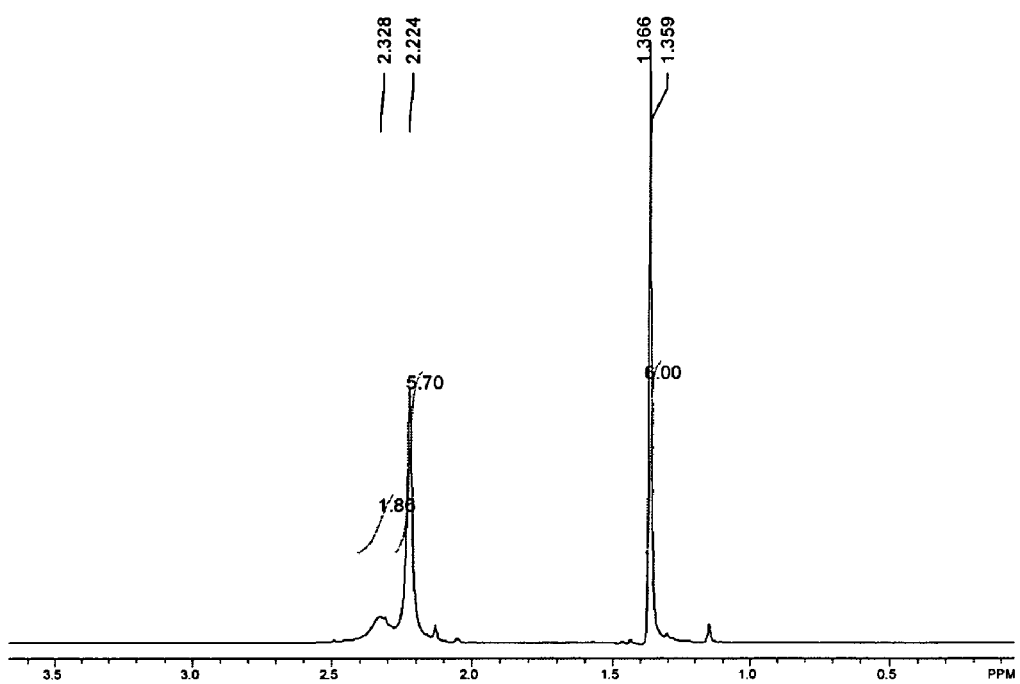

[Figure 2]
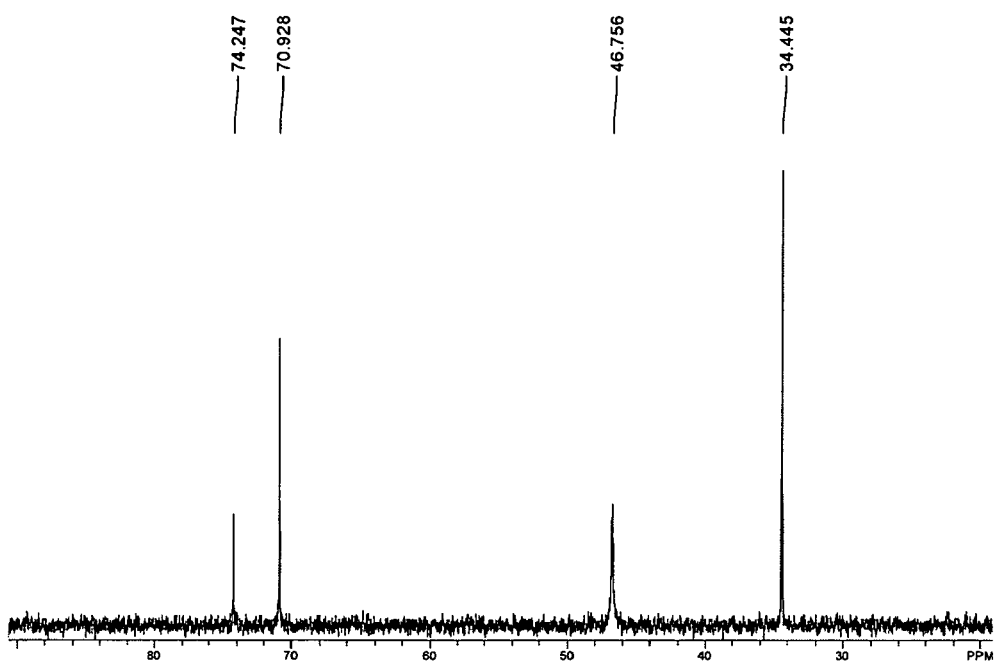

[Figure 3]
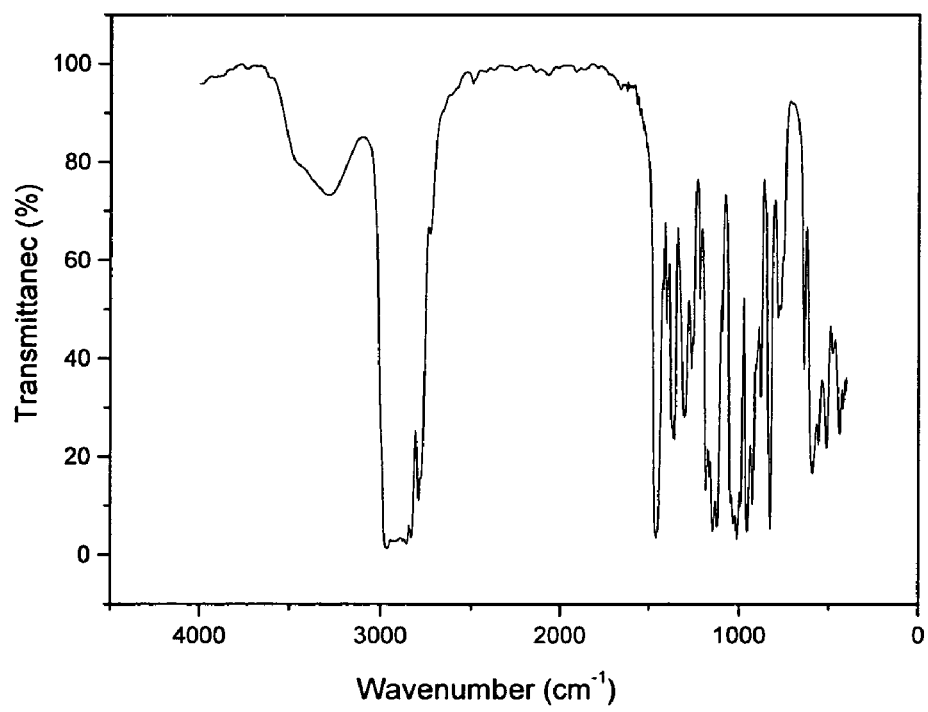

[Figure 4]
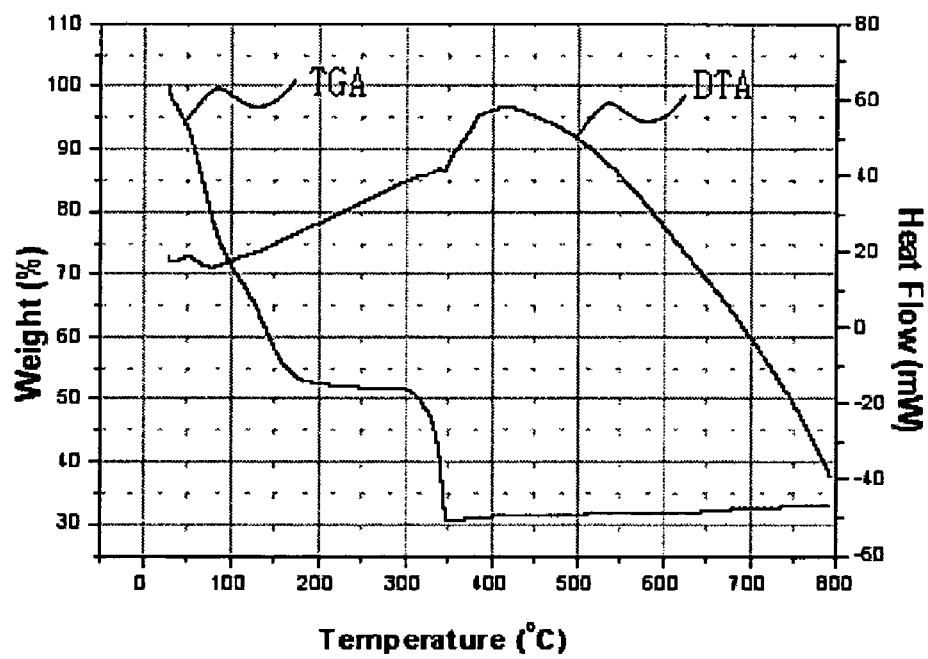

【Figure 5】
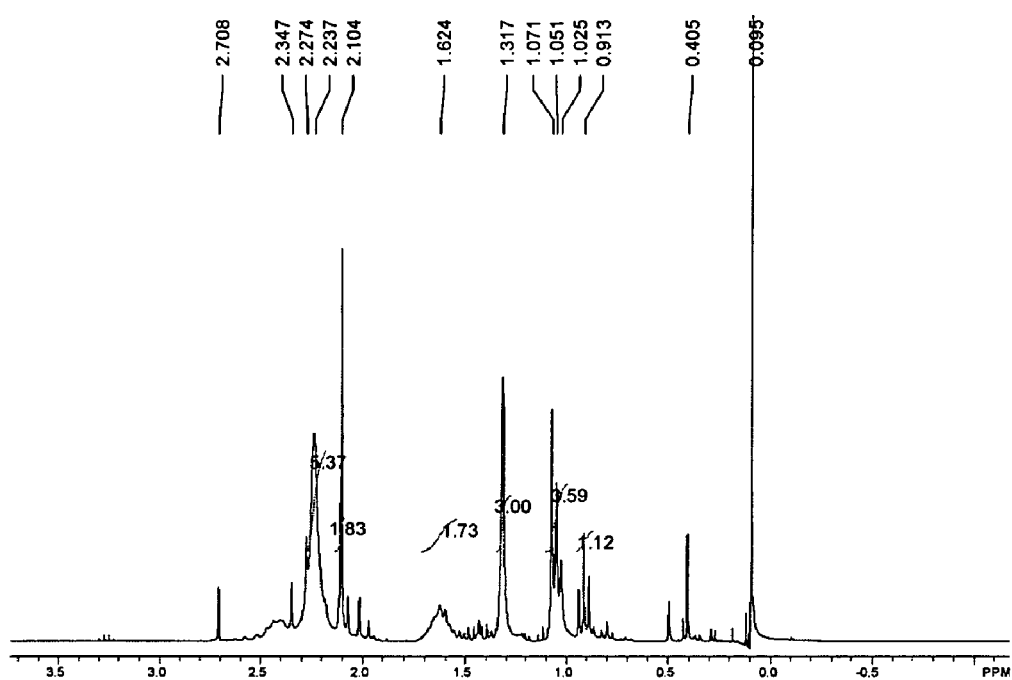

【Figure 6】
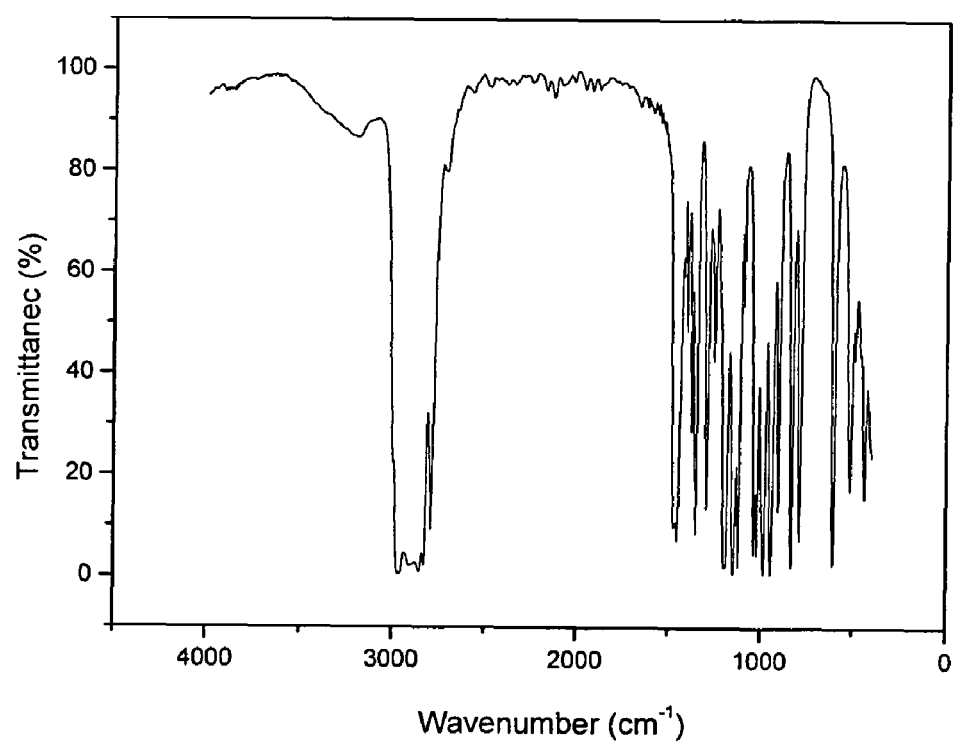

TIN AMINO-ALKOXIDE COMPLEXES AND PROCESS FOR PREPARING THEREOF

TECHNICAL FIELD

The present invention relates to novel tin amino-alkoxide complexes, more precisely tin amino alkoxide complexes useful as a precursor for tin and tin oxide thin films and for the production of nano-sized tin and tin oxide particles and a method for preparing the same.

BACKGROUND ART

Tin oxide was first reported in 1976 and is known as a transparent conductive oxide having visible light permeability, infrared reflectance and low resistance. Owing to such characteristics, tin oxide has widely been used for gas sensor, solar cell electrode and low resistant glass coating, etc. Many research groups are studying on tin alkoxide, amide, and chalcogenide compounds in the form of monomer, and having 2-coordinated or 4 coordinated structure. To produce tin, tin oxide, and materials containing tin, precursors such as $SnCl_4$, $Sn(CH_3)_4$, $(CH_3)_2SnCl_2$, $Sn(C_4H_9)_2(CHCOO)_2$, $Sn(OAc)_2$, $Sn(acac)_2$ (acac=acetylacetonate), and $Sn(XR)_2$ (X=O, S, N, R=Me, Et, i-Pr, t-Bu) have been used. All the synthetic compounds are stabilized by using a ligand having huge steric hindrance or by an electron donor substrate. The most common tin compounds are thermolysed in a vacuum chamber by MOCVD (metal organic chemical vapor deposition) process via unstable gas phase reaction at 80-450° C. This process is a method based on the decomposition of those compounds in gas phage which are reactive on a substrate as gas phase. But, the method is limited. Decomposition for the formation of thin film is too slow but if decomposition rate is accelerated, the quality of the thin film is reduced. Thin film can be produced by PCVD (plasma-induced chemical vapor deposition) and sputtering, but these methods have structural problem and quality problem of photoelectron (T. W. F. Russel, B. N. Baron and R. E. Rocheleau, *J. Vac. Sci. Technol.* B2(4), 1984, 840; Sanjay Mathur, Hao Shen, Vladimir Sivakov, and Ulf Werner, *Chem. Mater.* 2004, 16, 2449; Henry Gerung, Scott D. Bunge, Timothy J. Boyle, C. Jeffrey Brinkerab and Sang M. Han, *Chem. Commun.*, 2005, 1914; Seigi Suh and David M. Hoffman, *Inorg. Chem.* 1996, 35, 6164; A. Watanabe, M. Unno, F. Hojo, T. Miwa, *J. Mater. Sci. Lett.*, 2001, 20, 491; S. Veprek, J. Prokop, F. Glatz, and R. Merica, F. R. Klingan and W. A. Herrmann, *Chem. Mater.* 1996, 8, 825).

DISCLOSURE

Technical Problem

The present inventors developed a novel tin precursors useful for the preparation of tin and tin oxide, and tin containing substances at a lower temperature with improved thermo-stability and volatility but without contamination of carbon or halogen by introducing a novel ligand in order to coordinate dialkylamino group to tin.

It is an object of the present invention to provide a novel tin compound precursors with improved thermo-stability and volatility to generate high quality tin and tin oxide, and nano particles, and tin containing substances, and a method for preparing the same.

Technical Solution

To achieve the above object, the present invention provides tin amino-alkoxide complexes represented by formula 1.

$$Sn[O-A-NR^1R^2]_2 \qquad \text{[Formula 1]}$$

In formula 1, A is linear or branched (C2-C10) alkylene substituted or not substituted with halogen; $R^1$ and $R^2$ are independently linear or branched (C1-C7) alkyl substituted or not substituted with halogen.

The present invention also provides a method for preparing tin compounds using the said tin amino-alkoxide complexes as a precursor.

Hereinafter, the present invention is described in detail.

The tin complexes of formula 1 includes the tin amino alkoxide compounds represented by formula 2 ($A=$—$CR^3R^4(CH_2)_m$).

$$Sn[OCR^3R^4(CH_2)_m\text{—}NR^1R^2]_2 \qquad \text{[Formula 2]}$$

In Formula 2, m is an integer of 1-3; $R^1$ and $R^2$ are independently linear or branched (C1-C5) alkyl substituted or not substituted with F; $R^3$ and $R^4$ are independently linear or branched (C1-C5) alkyl substituted or not substituted with H or F.

Particularly, m is preferably 1 or 2, $R^1$ and $R^2$ are independently selected from the group consisting of $CH_3$, $CF_3$, $C_2H_5$, $CH(CH_3)_2$ and $C(CH_3)_3$, and $R^3$ and $R^4$ are independently selected from the group consisting of $CH_3$, $CF_3$, $C_2H_5$, $CH(CH_3)_2$ and $C(CH_3)_3$.

The tin amino alkoxide compounds of formula 1 of the present invention can be prepared by reacting the tin complexes of formula 3 with 2 equivalents of the amino alkoxide alkali metal salt compounds of formula 2 as shown in reaction formula 1.

$$SnX_2 + 2MO\text{-}A\text{-}NR^1R^2 \rightarrow Sn[O\text{-}A\text{-}NR^1R^2]_2 + 2MX \qquad \text{[Reaction Formula 1]}$$

$$Sn[O\text{-}A\text{-}NR^1R^2]_2 \qquad \text{[Formula 1]}$$

$$SnX_2 \qquad \text{[Formula 3]}$$

$$MO\text{-}A\text{-}NR^1R^2 \qquad \text{[Formula 4]}$$

In formula 1, formula 3 and formula 4, X is $N[Si(CH_3)_3]_2$, Cl, Br or I; M is H, Li, Na or K; A is linear or branched (C2-C10) alkylene substituted or not substituted with halogen; $R^1$ and $R^2$ are independently linear or branched (C1-C7) alkyl substituted or not substituted with halogen.

In the method for preparing tin amino alkoxide compounds of the present invention, the reaction solvent is not limited and any hydrocarbon solvent can be used. Particularly, ether, n-hexane, n-heptane, benzene, toluene or tetrahydrofurane (THF) or the mixture thereof is preferred.

The reaction temperature is preferably room temperature to 70° C. In fact, the reaction is completed in 2-10 hours at room temperature without heating.

The compounds of formula 1 (reaction product) was confirmed by nuclear magnetic resonance spectroscopy (NMR), Fourier transform infrared spectroscopy (FTIR), and elemental analysis (EA). The produced organic tin (II) compounds (amino-alkoxy tin (II) compound) are colorless liquid at room temperature, which are highly volatile compounds so that pure compounds can be easily obtained by fractional distillation at 100-120° C. at $10^{-2}$ torr. When these compounds are cooled down in liquid nitrogen, it turns into white solid compounds and when temperature is raised to room temperature it remains as solid compounds unless heated at more than 70° C.

Thermo-stability, volatility and decomposition temperature of the tin compounds prepared in this invention were analyzed by thermogravimetric analysis/differential thermal analysis (TGA/DTA).

The tin precursors of the present invention are in liquid phase at room temperature and can be purified as pure compounds by fractional distillation at 100-120° C. at $10^{-2}$ torr. These precursors can be used not only for the production of tin and tin oxide nano materials and tin containing alloy but also for the production of tin thin films by metal organic chemical vapor deposition (MOCVD).

According to the method described in Korean Patent No. 666759, thin film type or nano-particle type tin compounds can be produced by regulating particle size and shape by using the said tin amino alkoxide compounds as a precursor.

ADVANTAGEOUS EFFECT

As explained hereinbefore, the tin amino-alkoxide compounds of the present invention have high volatility and thermo-stability, so that they can be effectively used as a precursor for the production of tin nano-particles or applied in MOCVD to produce high quality metal films.

DESCRIPTION OF DRAWINGS

The above and other objects, features and advantages of the present invention will become apparent from the following description of preferred embodiments given in conjunction with the accompanying drawings, in which:

FIG. 1 is a diagram showing the result of $^1$H-NMR of the Sn(dmamp)$_2$ compound prepared in example 1.

FIG. 2 is a diagram showing the result of $^{13}$C-NMR of the Sn(dmamp)$_2$ compound prepared in example 1.

FIG. 3 is a diagram showing the result of FT-IR of the Sn(dmamp)$_2$ compound prepared in example 1.

FIG. 4 is a diagram showing the results of TGA and DTA of the Sn(dmamp)$_2$ compound prepared in example 1.

FIG. 5 is a diagram showing the result of $^1$H-NMR of the Sn(dmamb)$_2$ compound prepared in example 3.

FIG. 6 is a diagram showing the result of FT-IR of the Sn(dmamb)$_2$ compound prepared in example 3.

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

Every experiment was performed under inactive argon or nitrogen atmosphere using glove box or Schlenk line.

EXAMPLE 1

Preparation of
(dimethylamino-2-methyl-2-propoxy)Sn(II)
[Sn(dmamp)$_2$]

SnCl$_2$ (1 g, 5.27 mmol) and Lithium bistrimethylsilylamide[Li(btsa)] (1.76 g, 10.54 mmol) were added in 250 mL Schlenk flask at room temperature, to which ether (50 mL) was added, followed by stirring for 3 hours. The mixed solution was filtered to eliminate LiCl and the solvent was eliminated from the filtrate under vacuum condition. Fractional distillation was performed at 100° C. at $10^{-2}$ torr to obtain Sn(btsa)$_2$. Sn(btsa)$_2$ (1 g, 2.28 mmol) was dissolved in normal hexane. 2 Equivalent of dimethylamino-2-methyl-2-propanol (0.53 g, 4.56 mmol) was added thereto slowly at room temperature, followed by stirring for 6 hours.

After eliminating the solvent under vacuum condition, fractional distillation was performed at 100° C. at $10^{-2}$ torr to give pure Sn(dmamp)$_2$ compound (91%).

Element analysis for C$_{12}$H$_{28}$N$_2$O$_2$Sn.H$_2$O {calculated value (measured value)}: C, 39.05 (37.92); H, 8.19 (7.66); N, 7.59 (8.02).

The $^1$H-NMR of the Sn(dmamp)$_2$ compound prepared in example 1 is shown in FIG. 1, the $^{13}$C-NMR is shown in FIG. 2, and the FT-IR is shown in FIG. 3.

The TGA and DTA of the Sn(dmamp)$_2$ compound prepared in example 1 are shown in FIG. 4. As shown in FIG. 4, the (dimethylamino-2-methyl-2-propoxy)Sn(II) [Sn (dmamp)$_2$] compound of the present invention exhibited rapid loss of mass at the temperature range of 300-350° C.

EXAMPLE 2

Preparation of
(dimethylamino-2-methyl-2-propoxy)Sn(II)
[Sn(dmamp)$_2$]

SnBr$_2$ (1 g, 3.59 mmol) and Sodium dimethyl amino-2-methyl-2-propoxide[Na(dmamp)] (1 g, 7.18 mmol) were added in 250 mL Schlenk flask at room temperature, to which THF (50 mL) was added, followed by refluxing for 12 hours. The mixed solution was filtered to eliminate NaCl and the solvent was eliminated from the filtrate under vacuum condition. Fractional distillation was performed at 100° C. at $10^{-2}$ torr to give pure compound (93%).

Element analysis for C$_{12}$H$_{28}$N$_2$O$_2$Sn.H$_2$O {calculated value (measured value)}: C, 39.05 (37.92); H, 8.19 (7.66); N, 7.59 (8.02).

Therefore, it was confirmed that the compound which is the same as the compound of example 1 was prepared.

EXAMPLE 3

Preparation of
(dimethylamino-2-methyl-2-butoxy)Sn(II)
[Sn(dmamb)$_2$]

SnCl$_2$ (1 g, 5.27 mmol) Lithium bistrimethylsilylamide [Li(btsa)] (1.76 g, 10.54 mmol) were added in 250 mL Schlenk flask at room temperature, to which ether (50 mL) was added, followed by stirring for 3 hours. The mixed solution was filtered to eliminate LiCl and the solvent was eliminated from the filtrate under vacuum condition. Fractional distillation was performed at 100° C. at $10^{-2}$ torr to obtain Sn(btsa)$_2$. The Sn(btsa)$_2$ was dissolved in normal hexane. 2 equivalent of dimethylamino-2-methyl-2-butanol (0.59 g, 4.56 mmol) was added thereto slowly at room temperature, followed by stirring for 6 hours. After eliminating the solvent under vacuum condition, fractional distillation was performed at 120° C. at $10^{-2}$ torr to give pure Sn(dmamb)$_2$ compound (89%).

The $^1$H-NMR of the Sn(dmamb)$_2$ compound prepared in example 3 is shown in FIG. 5.

The FT-IR of the Sn(dmamb)$_2$ compound prepared in example 3 is shown in FIG. 6.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A tin amino-alkoxide complexes represented by formula 2:

$$Sn[OCR^3R^4(CH_2)_m—NR^1R^2]_2 \quad \text{[Formula 2]}$$

where in formula 2, m is an integer of 1-3;
$R^1$ and $R^2$ are independently linear or branched (C1-C7) alkyl substituted with halogen or not substituted, and
$R^3$ and $R^4$ are independently linear or branched (C1-C5) alkyl substituted with F or not substituted.

2. The tin amino-alkoxide complexes according to claim 1, wherein the complexes are represented by formula 2:

$$Sn[OCR^3R^4(CH_2)_m—NR^1R^2]_2 \quad \text{[Formula 2]}$$

In Formula 2, m is an integer of 1-3;
$R^1$ and $R^2$ are independently linear or branched (C1-C5) alkyl substituted with F or not substituted; and
$R^3$ and $R^4$ are independently linear or branched (C1-C5) alkyl substituted with F or not substituted.

3. The tin amino-alkoxide complexes according to claim 2, wherein the m of formula 2 is 1 or 2.

4. The tin amino-alkoxide complexes according to claim 2, wherein the $R^1$ and $R^2$ are independently selected from the group consisting of $CH_3$, $CF_3$, $C_2H_5$, $CH(CH_3)_2$ and $C(CH_3)_3$, and the $R^3$ and $R^4$ are independently selected from the group consisting of $CH_3$, $CF_3$, $C_2H_5$, $CH(CH_3)_2$ and $C(CH_3)_3$.

5. A method for preparing the tin amino-alkoxide complexes represented by formula 1 characterized by the reaction of the tin compound of formula 3 and the amino-alkoxide alkali metal salt compounds of formula 4:

$$Sn[O-A-NR^1R^2]_2 \quad \text{[Formula 1]}$$

$$SnX_2 \quad \text{[Formula 3]}$$

$$MO-A-NR^1R^2 \quad \text{[Formula 4]}$$

In formula 1, formula 3 and formula 4, X is $N[Si(CH_3)_3]_2$, Cl, Br or I;
M is H, Li, Na or K; A is linear or branched (C2-C10) alkylene substituted with halogen or not substituted; and
$R^1$ and $R^2$ independently linear or branched (C1-C7) alkyl substituted with halogen or not substituted.

6. A method for preparing a tin compound using one of the tin amino-alkoxide complexes of claim 1 as a precursor, comprising producing a tin compound from the tin amino-alkoxide complex.

7. A tin compound prepared by the method of claim 6.

8. The tin compound according to claim 7, wherein the tin compound is a tin oxide thin film or a tin oxide nano-particle.

* * * * *